United States Patent
Fogarty et al.

(10) Patent No.: US 10,928,261 B2
(45) Date of Patent: *Feb. 23, 2021

(54) SYSTEM AND METHOD FOR ANALYSING VAPOUR PRESSURE

(71) Applicant: Icon Scientific Limited, Bath (GB)

(72) Inventors: Kevin Fogarty, Somerset (GB); David Hope, Surrey (GB); Dave Thompson, Bristol (GB); Bob Birchmore, Bury (GB)

(73) Assignee: Icon Scientific Limited, Bath (GB)

( * ) Notice: Subject to any disclaimer, the term of this patent is extended or adjusted under 35 U.S.C. 154(b) by 162 days.

This patent is subject to a terminal disclaimer.

(21) Appl. No.: 15/988,301

(22) Filed: May 24, 2018

(65) Prior Publication Data

US 2018/0372570 A1 Dec. 27, 2018

Related U.S. Application Data

(63) Continuation of application No. 14/777,165, filed as application No. PCT/GB2014/050843 on Mar. 17, 2014, now Pat. No. 9,983,079.

(30) Foreign Application Priority Data

Mar. 15, 2013 (GB) .................................... 1304704

(51) Int. Cl.
*G01L 7/16* (2006.01)
*G01N 7/14* (2006.01)
(Continued)

(52) U.S. Cl.
CPC ................ *G01L 7/16* (2013.01); *B60K 23/00* (2013.01); *B60W 30/14* (2013.01);
(Continued)

(58) Field of Classification Search
CPC ... G01L 19/147; G01L 9/0042; G01L 9/0054; G01L 9/0072; G01L 13/025; G01L 19/04;
(Continued)

(56) References Cited

U.S. PATENT DOCUMENTS 4,393,689 A 7/1983 Renon et al.
4,783,989 A * 11/1988 Reed ........................ G01N 7/14
73/64.45
(Continued)

FOREIGN PATENT DOCUMENTS

FR 2572530 A1 5/1986
WO 9400671 A1 1/1994

OTHER PUBLICATIONS

Communication pursuant to Article 94(3) EPC for EP 14 715 646.7 dated Sep. 5, 2018, 6 pp.
(Continued)

*Primary Examiner* — Andre J Allen
(74) *Attorney, Agent, or Firm* — Lathrop GPM LLP

(57) ABSTRACT

An apparatus for measuring the vapour pressure of a liquid hydrocarbon sample is disclosed. The apparatus comprises a sealed chamber (25) for receiving the sample. The chamber (25) is at least partially defined by a moveable element (26) such that moving the moveable element (26) alters the volume of the chamber (25). The apparatus comprises a displacement sensor (29) configured to measure a displacement of the movable element (26).

15 Claims, 6 Drawing Sheets

(51) Int. Cl.
*B60W 30/14* (2006.01)
*B60K 23/00* (2006.01)
*G01D 5/28* (2006.01)
*G01N 33/24* (2006.01)

(52) U.S. Cl.
CPC ............ *B60W 30/143* (2013.01); *G01D 5/28* (2013.01); *G01N 7/14* (2013.01); *G01N 33/24* (2013.01)

(58) Field of Classification Search
CPC . G01L 19/14; G01L 19/0038; G01L 19/0084; G01L 9/0075; G01L 19/0069; G01L 19/0618; G01L 9/0055; G01L 9/0073; G01L 19/0092; G01L 19/0645; G01L 19/143; G01L 9/0051; G01L 9/0052; G01L 19/0007; G01L 19/0046; G01L 19/06; G01L 19/0627; G01L 19/0681; G01L 27/002; G01L 9/00; G01L 9/0041; G01L 9/0044; G01L 11/025; G01L 11/04; G01L 19/0023; G01L 19/0672; G01L 19/069; G01L 19/142; G01L 19/16; G01L 7/00; G01L 7/163; G01L 7/166; G01L 9/0047; G01L 9/12; G01L 11/02; G01L 13/00; G01L 15/00; G01L 19/003; G01L 19/0609; G01L 19/083; G01L 19/10; G01L 19/145; G01L 19/148; G01L 27/005; G01L 7/08; G01L 7/082; G01L 9/0045; G01L 9/0048; G01L 9/006; G01L 9/007; G01L 9/0076; G01L 9/04; G01L 9/045; G01L 9/06; G01L 9/065; G01L 9/125; G01L 11/00; G01L 17/00; G01L 19/00; G01L 19/0015; G01L 19/0076; G01L 19/02; G01L 19/08; G01L 19/141; G01L 19/146; G01L 1/142; G01L 1/2262; G01L 1/246; G01L 21/12; G01L 23/16; G01L 27/007; G01L 7/04; G01L 7/063; G01L 7/084; G01L 7/086; G01L 7/16; G01L 9/0002; G01L 9/0007; G01L 9/0016; G01L 9/0019; G01L 9/0022; G01L 9/0027; G01L 9/0033; G01L 9/0039; G01L 9/005; G01L 9/0058; G01L 9/0077; G01L 9/0079; G01L 9/008; G01L 9/0092; G01L 9/0095; G01L 9/025; G01L 9/08; G01L 9/085; G01L 9/105; G01L 9/14; G01L 9/16; G01N 25/60; G01N 27/223; G01N 33/24; G01N 7/00; G01N 7/14

See application file for complete search history.

(56) References Cited

U.S. PATENT DOCUMENTS

| | | | |
|---|---|---|---|
| 5,123,817 | A | 6/1992 | Willemsen |
| 5,172,586 | A | 12/1992 | Reed |
| 5,563,339 | A | 10/1996 | Compton et al. |
| 5,635,631 | A | 6/1997 | Yesudas et al. |
| 6,763,731 | B1 | 7/2004 | Padden |
| 7,111,757 | B1 | 9/2006 | O'Brien et al. |
| 2003/0150259 | A1 | 8/2003 | Unger et al. |
| 2012/0266663 | A1 | 10/2012 | Benet et al. |

OTHER PUBLICATIONS

PCT Patent Application PCT/GB2014/050843 International Search Report and Written Opinion dated Jun. 10, 2014, 11 pages.
Non-Final Rejection in U.S. Appl. No. 14/777,165 dated Aug. 15, 2017, 11 pp.

\* cited by examiner

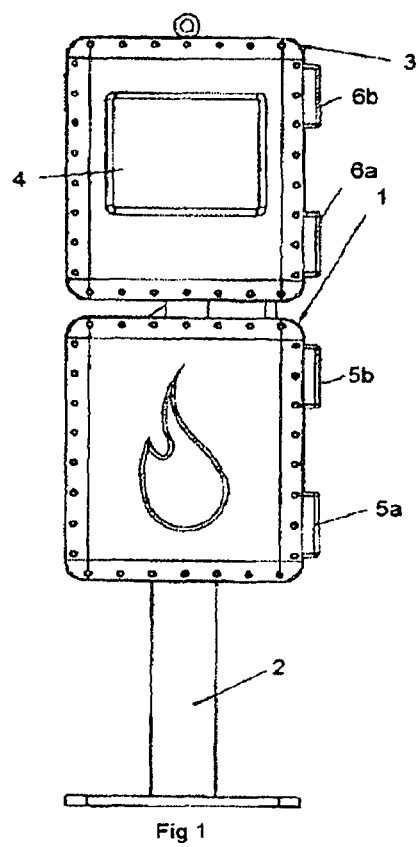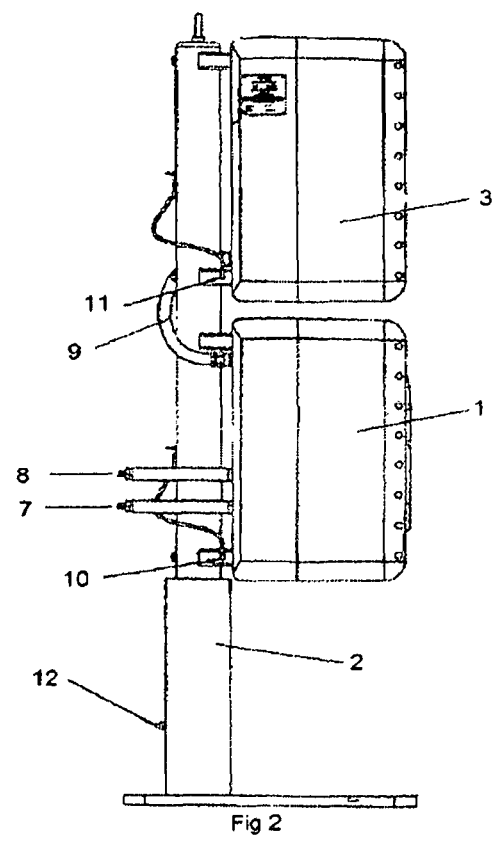
Fig 1
Fig 2

SYSTEM AND METHOD FOR ANALYSING VAPOUR PRESSURE

RELATED APPLICATIONS

The present Application is a continuation of U.S. patent application Ser. No. 14/777,165, filed Sep. 15, 2015, which is a national stage entry of Patent Cooperation Treaty Application Number PCT/GB2014/050843, filed Mar. 17, 2014, which claims priority to Great Britain Patent Application Number 1304704.8, filed Mar. 15, 2013. Each of the afore-mentioned applications is incorporated herein by reference.

FIELD OF THE INVENTION

The present invention concerns apparatus and methods for measuring the vapour pressure of hydrocarbons. In particular, but not exclusively, the invention concerns apparatus and methods for measuring the vapour pressure of hydrocarbons online in chemical plants or refineries.

BACKGROUND OF THE INVENTION

Vapour pressure is a well-known parameter related to the volatility of a substance. The vapour pressure is the pressure of a gaseous substance in equilibrium with the condensed substance in a closed system at a fixed temperature.

Vapour pressure can be measured using many standard methods. Examples of standard methods for measuring hydrocarbon vapour pressures include ASTM D6377: Determination of Vapour Pressure of Crude Oil: VPCRx (Expansion Method); ASTM D6378: Determination of Vapour Pressure (VPX) of Petroleum products, Hydrocarbons, and Hydrocarbon-Oxygenate mixtures (Triple Expansion Method); and ASTM D6897: Vapour Pressure of Liquefied Petroleum Gases (LPG) (Expansion Method). Results from vapour pressure analyses can also be correlated back to Reid Vapour Pressure and others by the use of published and accepted correlation factors. Correlated test methods include ASTM D323: Standard Test Method for Vapour Pressure of Petroleum products (Reid Method); ASTM D4953: Standard Test Method for Vapour Pressure of Gasoline and Gasoline-Oxygenate Blends (Dry Method); ASTM D5190: Standard Test Method for Vapour Pressure of Petroleum Products (Automatic Method); ASTM D5191: Standard Test Method for Vapour Pressure of Petroleum Products (Mini Method); ASTM D5188: Standard Test Method for Vapour-Liquid Ratio Temperature Determination of Fuels (Evacuated Chamber Method); and ASTM D5482: Standard Test Method for Vapour Pressure of Petroleum Products (Mini Method—Atmospheric).

Methods such as those above have typically been carried out in a system in which a sample is placed into a sealed chamber and a piston withdrawn so as to expand the volume of the chamber. Because the chamber is sealed, the expansion results in a known volumetric ratio of liquid to vapour. After a pause to allow the system to equilibrate, the pressure in the chamber is measured. From the known vapour/liquid ratio and the measured pressure, the vapour pressure can be calculated. The chamber may be expanded once or multiple times, depending on the method in question. The movement of the piston, and hence the expansion of the chamber, is controlled by using a stepper-motor to drive the piston. Stepper-motors offer control of motion in small, discrete steps. While this can produce fine control of the motion of the piston, it would be desirable to provide more precise determination of the motion so as to produce a more accurate measurement.

Vapour pressure measurements of hydrocarbons may be carried out in chemical plants such as refineries. The measurements can be carried out by taking a sample to a laboratory but doing so results in a delay in obtaining the data. A method of taking online measurements is therefore desirable. However, refineries often include zones with potentially explosive atmospheres so online measurements need to be safe for use in such zones.

The present invention seeks to mitigate the above-mentioned problems. Alternatively or additionally, the present invention seeks to provide improved apparatus and methods for measuring the vapour pressure of hydrocarbons.

SUMMARY OF THE INVENTION

According to a first aspect of the invention, there is provided an apparatus for measuring the vapour pressure of a liquid hydrocarbon sample, the apparatus comprising a sealed chamber for receiving the sample; wherein the chamber is at least partially defined by a moveable element such that moving the moveable element alters the volume of the chamber; wherein the apparatus comprises a displacement sensor configured to measure a displacement of the movable element.

Many standard methods for measuring vapour pressure require the use of an expanding chamber. Such a chamber should be sealed so that the measurement is made in a closed system. It will be appreciated that the sealed chamber may include inputs and outputs that are closed by a valve when the measurement is in progress, thus resulting in a sealed chamber, but that can be opened to flush the chamber and introduce a new sample between measurements. The accuracy of the vapour pressure measurement depends in part on the accuracy of the expansion. Prior art systems have relied on the drive mechanism for the movable element to control and measure the expansion. For example, stepper motors have been used to move the moveable element, with the stepper motor being instructed to move the element a fixed distance. By using a displacement sensor to measure the displacement of the moveable element, the accuracy of the expansion, and thus of the final measurement, can be improved.

It may be that the displacement sensor is a capacitive displacement sensor, an eddy current displacement sensor, an inductive displacement sensor, a magneto-inductive displacement sensor, a laser displacement sensor or a draw-wire displacement sensor. Preferably the displacement sensor is a non-contact displacement sensor. More preferably the displacement sensor is a laser displacement sensor, for example a laser triangulation sensor or a laser range finder. A non-contact sensor may operate reliably for long periods of time without maintenance. It will be appreciated that vapour pressure analysis may be required as part of a process where the time between maintenance shuts-down is desirably as long as possible whilst providing for safe operation. The reliability of components may therefore be a critical factor.

Preferably the apparatus can be operated so as to produce measurements according to the following test methods:

ASTM D6377: Determination of Vapour Pressure of Crude Oil: VPCRx (Expansion Method);

ASTM D6378: Determination of Vapour Pressure (VPX) of Petroleum products, Hydrocarbons, and Hydrocarbon-Oxygenate mixtures (Triple Expansion Method); and ASTM D6897: Vapour Pressure of Liquefied Petroleum Gases (LPG) (Expansion Method).

Preferably the apparatus can be operated so as to produce measurements according to the correlated test methods:

ASTM D323: Standard Test Method for Vapour Pressure of Petroleum products (Reid Method);

ASTM D4953: Standard Test Method for Vapour Pressure of Gasoline and Gasoline-Oxygenate Blends (Dry Method);

ASTM D5190: Standard Test Method for Vapour Pressure of Petroleum Products (Automatic Method);

ASTM D5191: Standard Test Method for Vapour Pressure of Petroleum Products (Mini Method);

ASTM D5188: Standard Test Method for Vapour-Liquid Ratio Temperature Determination of Fuels (Evacuated Chamber Method); and ASTM D5482: Standard Test Method for Vapour Pressure of Petroleum Products (Mini Method—Atmospheric).

Preferably, the moveable element is a piston and the chamber is formed by the piston and a receptacle in which the piston is fitted so as to form a seal between the piston and the receptacle. For example, the receptacle may be a barrel in which the piston moves and which is closed off at the distal end so as to create a chamber at the distal end of the barrel with the size of the chamber being determined by the position of the piston. The piston is fitted so as to form a seal between the receptacle and the piston so as to form the sealed chamber. The seal may be achieved by a close fit of the piston in the receptacle but is preferably achieved by using an O-ring around the piston to create the seal between the piston and the receptacle. A piston may be advantageous because the piston permits the chamber size to be varied using a one-dimensional translation. That may combine well with the use of a displacement sensor, which may be highly accurate at measuring such a one-dimensional translation. Thus, the combination of a piston arrangement with a displacement sensor may result in a particularly accurate expansion and a particularly accurate vapour pressure measurement as a result.

It may be that the seal between the piston and the receptacle is formed by an O-ring around the piston. However, in some applications, the seal is preferably formed by two O-rings around the piston and spaced apart along the length of the piston. Such a 'double O-ring' arrangement may allow higher vapour pressures such as the vapour pressures of liquid petroleum gas (LPG) to be measured by forming a high-pressure seal.

Preferably the apparatus is equipped with an internal sample stirrer, located within the sealed chamber, to agitate the sample being analysed. Agitating the sample may reduce the time to equilibrium, which may be particularly important for more viscous samples which are reluctant to release the volatile components, e.g. crude oils. Preferably the stirrer comprises a magnetic stirrer, for example a magnetic stirrer bar, located inside the sealed chamber and a motor external to the sealed chamber. The motor drives at least one magnet, for example a pair of magnets, which in turn cause the magnetic stirrer to rotate. The motor preferably runs at between 55 and 65 rpm, for example 60 rpm. The operation of the motor is preferably programmable, for example to be controlled by the software that controls the measurement process. Thus the motor can be enabled or disabled during the equilibrium cycle. Preferably the user can also define the stirring time.

While the moveable element may be adjusted manually to expand the chamber, the apparatus preferably comprises a motor configured to drive the moveable element and a controller configured to receive a signal from the displacement sensor and to control the motor in response to the signal. The motor may be a linear actuator. Preferably the motor is a stepper motor. It will be appreciated that the ability to take frequent online measurements of a process may allow significant improvements in process control and it is therefore desirable that the apparatus can be used to take automatic measurements without the need for manual input. Prior art systems have used a motor to control the movement of the piston, but such systems are limited in their accuracy. By including the displacement sensor and linking that to a motor controller, the benefits of automatic measurements using the motor can be combined with the improved accuracy of the displacement sensor system.

Where a laser displacement sensor is used it may be that the laser displacement sensor measures the displacement of the moveable element directly. For example, the laser may be directed to reflect from a surface of the moveable element. However, preferably the apparatus comprises a laser reflector plate coupled to the moveable element and the laser displacement sensor is configured to measure a displacement of the laser reflector plate so as to measure the displacement of the movable element. Use of a laser reflector plate may permit more convenient alignment of the laser. In particular, the moveable element may be mounted on a motor and it may therefore not be convenient to arrange the laser displacement sensor so as to reflect off the moveable element itself without the motor blocking the laser beam.

Preferably the apparatus comprises a device for monitoring the temperature of the chamber and a temperature control apparatus to heat or cool the chamber. It may be that the temperature control apparatus comprises a heater, for example a cartridge heater. It may be that the temperature control apparatus comprises a cooler, for example a Peltier cooler. Preferably the temperature control apparatus comprises a cooler and a heater. In some embodiments the temperature control apparatus may be a combined heater and cooler. It will be appreciated that a vapour pressure measurement is made at a temperature. Therefore it is desirable to control the temperature of the chamber. That may be achieved by controlling the environment around the apparatus, for example by immersing the apparatus in a water or oil bath, but such an approach may not be desirable for electrical or optical reasons. By using a device, such as a thermocouple or resistance temperature detector (RTD), to monitor the temperature of the chamber and providing a heater, such as a cartridge heater, and a cooler, such as a Peltier cooler, to heat or cool the chamber, the temperature of the chamber can be controlled independently of the environment. That may be particularly advantageous where the apparatus is used online in the field as the environment in the field may vary considerably more than if, say, the apparatus was used in a laboratory. Preferably the device for monitoring the temperature of the chamber is located within the moveable element. Preferably the apparatus comprises a pressure sensor to measure the pressure in the chamber, wherein the pressure sensor is located within the moveable element. There may be electronics associated with the pressure sensor, the electronics being located within the moveable element. Locating the electronics and sensors within the moveable element may allow them to be in a more stable temperature environment and may allow for easy upgrades of the sensors by substitution of the moveable element.

Advantageously the apparatus is contained within an explosion-proof housing, for example an explosion-proof box. The skilled person will appreciate that an explosion-proof housing is one that prevents potential ignition sources, such as sparks, flames or explosions, within the housing escaping to the outside environment. For example, the housing may have a robust construction so as not to fail in the event of an explosion within the housing and inlets to the housing may be provided with breathing and draining devices, or flame arrestors, that prevent a flame from exiting the housing. In that way the apparatus can be used in areas with a potentially explosive atmosphere such as oil refineries to provide online monitoring of a process. If the displacement sensor is a non-contact, for example laser, device with good reliability, the explosion proof housing may need opening less frequently for maintenance. It will be appreciated that opening the explosion-proof housing may require special precautions so as not to ignite a potentially explosive atmosphere surrounding the housing.

For example, the apparatus contained within the explosion-proof housing may be rated in the following gas groups and temperatures classes: IIA T2, IIA T3, IIB T3, IIB+$H_2$ T4, T85° C. for Dust only environments or T300° C. The explosion proof housing may comprise breathing and draining devices to act as flame arrestors where samples or utilities enter or leave the explosion-proof housing. The apparatus may comply with standards IEC 60079-0: 2007-10 Explosive atmospheres—Part 0: Equipment—General requirements, IEC 60079-1: 2007-04 Explosive atmospheres—Part 1: Equipment protection by flameproof enclosures "d" and IEC 60079-31: 2008 Explosive atmospheres—Part 31: Equipment dust ignition protection by enclosure "t".

Preferably the apparatus is provided with a touch-screen interface, which is preferably mounted on an explosion-proof housing. In that way a large number of tasks can be carried out using the versatility of the touch-screen interface without having to open the explosion proof housing. The touch-screen may be provided on the explosion-proof housing in which the apparatus is contained but is preferably provided in a second explosion proof housing with connections, for example wired or wireless communications connections, to the first explosion-proof housing in which the apparatus is contained. Such an arrangement may allow for cheaper manufacture of a range of instruments and analysers as the second housing may be common between a large number of analyser products.

According to a second aspect of the invention there is provided a method of measuring the vapour pressure of a liquid hydrocarbon sample, the method comprising:
a. feeding the sample into a sealed chamber, wherein the chamber is at least partially defined by a moveable element;
b. expanding the chamber by displacing the moveable element by a displacement; and
c. measuring the pressure in the chamber; wherein the displacing of the moveable element includes measuring the displacement with a displacement sensor.

Preferably the displacing of the moveable element is controlled by measuring the displacement with the displacement sensor.

Preferably the moveable element is a piston and the chamber is formed by the piston and a receptacle in which the piston is fitted so as to form a seal between the piston and the receptacle.

Preferably the moveable element is driven by a motor and a controller receives a signal from the displacement sensor and controls the motor in response to the signal.

Preferably the displacement sensor is a non-contact displacement sensor.

More preferably the displacement sensor is a laser displacement sensor, for example a laser triangulation sensor or a laser range finder. Preferably a laser reflector plate is coupled to the moveable element and the laser displacement sensor measures a displacement of the laser reflector plate so as to measure the displacement of the movable element.

Preferably the method comprises monitoring the temperature of the chamber and operating a heater or a cooler to maintain the temperature at a desired value. Preferably the temperature is monitored using a device located within the moveable element. Preferably the pressure is measured using a pressure sensor located within the moveable element.

Preferably the method comprises stirring the sample between steps b and c. Preferably the stirring step is performed so as to allow the equilibrium to be reached within the sealed chamber.

Preferably the method embodies the ASTM D6377 "Determination of Vapour Pressure of Crude Oil: VPCRx (Expansion Method)" laboratory test in an on-line process analyser.

ASTM D6377 is a relatively new test method designed to overcome the limitations of the classic ASTM D323 "Standard Test Method for Vapour Pressure of Petroleum products (Reid Method)" (RVP) when applied to crude oil. ASTM D323 requires all measurements to be carried out at 100° F. (37.8° C.) and at a 4:1 vapour:liquid ratio. The ASTM D323 procedure also allows loss of volatile components during sampling and handling. With ASTM D6377 the vapour liquid ratio and measurement temperature is not fixed. Measurements at temperatures up to 100° C. and at Vapour:Liquid ratios from 0.02:1 to 4:1 are permissible. Hence the term VPCRx where x is the Vapour:Liquid ratio.

Because ASTM D323 is a well-established method and in many cases still remains the reference test D6377 recognises measurement at 100° F. (37.8° C.) and at a 4:1 Vapour:Liquid ratio as a specific case. D6377 allows calculation of a Reid Vapour Pressure Equivalent (RVPE) result from D6377 Vapour pressure measurements carried out at 100° F. (37.8° C.) and at a 4:1 Vapour:Liquid ratio. The calculation involves multiplying the D6377 result by a factor that is less than unity (D323 results are lower than raw ASTM D6377 due to loss of volatile components). As the RVPE measurement is still currently of major importance all of the precision and bias statements given in D6377 were determined under the D323 RVP test conditions.

D6377 also recognises measurement at 0.02:1 as a special case as this provides an indication of True Vapour Pressure (TVP). TVP is an ill-defined term and is not covered by any specific test method. The American Petroleum Institute (API) has, in the past, published a calculation to convert crude oil RVP to a "TVP" result at temperatures other than 100° F. (37.8° C.). This calculation is based on a "typical" crude oil and while still used is considered not to always be a reliable indicator of how much pressure could build up in a storage tank or what the bubble point pressure of a crude oil might be. This is because, as mentioned earlier, the small amounts of very volatile components present in the crude oil are lost during the RVP test. In storage tanks that are typically filled to 98%, these volatile components are concentrated in the small headspace and can develop much higher pressures than those predicted from RVP measurements. D6377 does not lose volatiles so measurement of vapour pressure at 0.02:1 (which corresponds to a 98% full tank) gives a more reliable estimate of the pressure that could build up in a tank headspace.

We have found that actual measurement at 0.02:1 has proved to be subject to poor repeatability. More reliable results have been obtained by measuring vapour pressure at a number of different vapour liquid ratios and extrapolating the curve obtained back to 0.02:1 or other Vapour:Liquid ratio. The vapour pressure vs Vapour:Liquid ratio curve preferably also allows determination of Gas Oil Ratio (GOR). GOR is typically defined as the Vapour:Liquid ratio at which the sample exhibits a vapour pressure of 14.7 psia (i.e. atmospheric pressure). This gives an indication of how much gas could potentially be released to the atmosphere in the case of oil spillage and GOR is used by the Environmental Protection Agency (EPA) for such estimates. GOR will vary with temperature but is normally estimated at 100° F. (37.8° C.)

Preferably the method performs at least one, and preferably all, of the following measurements:

1. Reid Vapour Pressure Equivalent (RVPE)

The RVPE method preferably comprises measuring vapour pressure at 4 expansion ratios (equivalent to Vapour:Liquid ratios) culminating in a final expansion of 4:1. With the measuring temperature at 100° F. (37.8° C.) the vapour pressure result at the final 4:1 expansion ratio is used (by application of the factors given in D6377) to calculate RVPE. Preferably the RVPE has a dedicated 4-20 Ma output on the apparatus.

2. True Vapour Pressure/Bubble Point Pressure (TVP/BPP)

The TVP/BPP method preferably uses the vapour pressure results measured as part of the RVPE method above. A curve fitting algorithm is used to estimate the vapour pressure at Vapour:Liquid ratios between 0.02:1 and 4:1. At 0.02 this result can be taken as a practical estimate of TVP and bubble point pressure (BPP). The TVP/BPP result preferably has a dedicated 4-20 Ma output on the apparatus.

3. Gas Oil Ratio (GOR)

The GOR method preferably uses the same curve fitting algorithm and vapour pressure results as the TVP/BPP method. Using the curve fitting algorithm, the expansion ratio at which the sample has a vapour pressure of 14.7 psia is determined to measure GOR. Like the other measured parameters GOR preferably has its own dedicated 4-20 Ma output on the apparatus.

For RVPE measurements to be valid the measuring temperature must be 100° F. (37.8° C.). However D6377 allows for measurements at temperatures other than this. The method of the invention is preferably carried out at temperatures between 5-60° C.

Thus, in an especially preferred aspect of the invention there is provided a method of measuring the RVPE, TVP/BPP and GOR of a liquid hydrocarbon sample, the method comprising:

a. feeding the sample into a sealed chamber, wherein the chamber is at least partially defined by a moveable element;

b. expanding the chamber by displacing the moveable element by a first displacement corresponding to a first expansion ratio;

c. measuring the pressure in the chamber as a first pressure result;

d. expanding the chamber by displacing the moveable element by a second displacement corresponding to a second expansion ratio;

e. measuring the pressure in the chamber as a second pressure result;

f. expanding the chamber by displacing the moveable element by a third displacement corresponding to a third expansion ratio;

g. measuring the pressure in the chamber as a third pressure result;

h. expanding the chamber by displacing the moveable element by a fourth displacement corresponding to a fourth expansion ratio, the fourth expansion ratio preferably being a 4:1 vapour:liquid ratio;

i. measuring the pressure in the chamber as a fourth pressure result;

j. using the fourth pressure result to calculate the RVPE;

k. using a curve fitting algorithm to create a pressure versus expansion ratio curve fitted to the first, second, third and fourth pressure results;

l. using the curve to predict a pressure at a vapour:liquid expansion ratio of 0.02:1 and reporting the predicted pressure as the TVP/BPP; and m. using the curve to predict a vapour:liquid expansion ratio at a pressure of 14.7 psia and reporting the predicted vapour:liquid expansion ratio as the GOR.

Preferably the method comprises measuring each of the displacements with a displacement sensor. Preferably the method comprises agitating the sample using a stirrer inside the sealed chamber between each of the expansion and measuring steps (i.e. as a step after each expansion and before each measurement). Preferably the stirrer is a magnetic stirrer driven by at least one magnet attached to a motor external to the sealed chamber. Preferably the agitating step is continued until a stable pressure measurement is recorded. It may be that the agitating step is continued for a predetermined time selected so as to result in a stable pressure measurement being recorded.

Whilst it is most preferable for the method to determine all of the RVPE, TVP/BPP and GOR, it will be appreciated that it is within the scope of the invention to measure at least one of the RVPE, TVP/BPP and GOR. Thus the method of the invention may comprise steps a to i above followed by at least one of:

step j;

steps k and l; and steps k and m.

It will be appreciated that in some circumstances in may be desirable to perform some calibration corrections or other adjustments when reporting the data measured by the device, for example to correct for temperature variations or other factors. Such adjustments may be performed as part of the pressure measuring steps c, e, g and i above. They may also be performed as part of the prediction in steps l and m. However, the may also be performed as part of the reporting of the results. Thus it may be that the reporting of a result comprises using the result to report a value, for example using the vapour:liquid expansion ratio at a pressure of 14.7 psia to report a value for GOR, or using the pressure at a vapour:liquid expansion ratio of 0.02:1 to report a value for TVP/BPP.

Preferably the method comprises measuring the properties (for example at least one, and preferably all, of the RVPE, TVP/BPP and GOR) of multiple liquid hydrocarbon samples. It will be appreciated that cleaning the sealed chamber between measurements of different samples is important in order to obtain reliable results. Flushing fluid or validation fluid, such as pure compounds, for example 99.5% n-Hexane, can be used to flush the sealed chamber. Preferably the method includes flushing the sealed chamber between measurements of a first and second sample. Preferably the sealed chamber comprises an inlet and an outlet and the samples are fed into the sealed chamber from a sample line, for example tubing connected to a sampling device in a process flow, via the inlet and the flushing comprises:
  a. closing the inlet and opening the outlet;
  b. contracting the sealed chamber by displacing the moveable element, preferably so as to reduce the volume of the sealed chamber to substantially zero;
  c. opening the inlet and closing the outlet;
  d. expanding the sealed chamber by displacing the moveable element, so as to draw fluid from a flush line, for example a line from a reservoir of pure compound, into the sealed chamber, wherein before the expansion takes place a valve upstream of the sealed chamber is operated so as to switch the input from the sample line to the flush line;
  e. closing the inlet and opening the outlet;
  f. contracting the sealed chamber by displacing the moveable element, preferably so as to reduce the volume of the sealed chamber to substantially zero;
  g. repeating steps c to f, for example 6 to 10 times; and operating the valve upstream of the sealed chamber so as to switch the input back to the sample line from the flush line.

In some embodiments step a may be omitted, for example if there is sufficient upstream pressure to prevent reverse flow in the sample line, however step a is preferably present.

It will be appreciated that operating the valve upstream of the sealed chamber so as to switch the input from the sample line to a flush line is done before the first step in which flush fluid is drawn into the chamber. However, the operating can be done at any time during, between or after the first three steps above and that operation is sufficient for the valve to have been operated before all of the repeated steps of expanding the sealed chamber by displacing the moveable element so as to draw fluid from the flush line into the sealed chamber.

Preferably the step of expanding the sealed chamber by displacing the moveable element so as to draw fluid from the flush line into the sealed chamber comprises drawing a volume of between 5 and 15 ml, for example 10 ml, of flushing fluid into the sealed chamber. Preferably the total volume of flushing fluid used cleaning the sealed chamber between measurements of different samples is less than 100 ml. That may be significantly less than the volume used if, for example, the chamber is flushed by forcing flushing fluid through the chamber under pressure from an external reservoir.

It will of course be appreciated that features described in relation to one aspect of the present invention may be incorporated into other aspects of the present invention. For example, the method of the invention may incorporate any of the features described with reference to the apparatus of the invention and vice versa.

DESCRIPTION OF THE DRAWINGS

Embodiments of the present invention will now be described by way of example only with reference to the accompanying schematic drawings of which:

FIG. 1 is a front view of an apparatus according to a first embodiment of the invention in closed explosion proof boxes;

FIG. 2 is a side view of the apparatus of FIG. 1 with the boxes closed;

DETAILED DESCRIPTION

Figure 3:
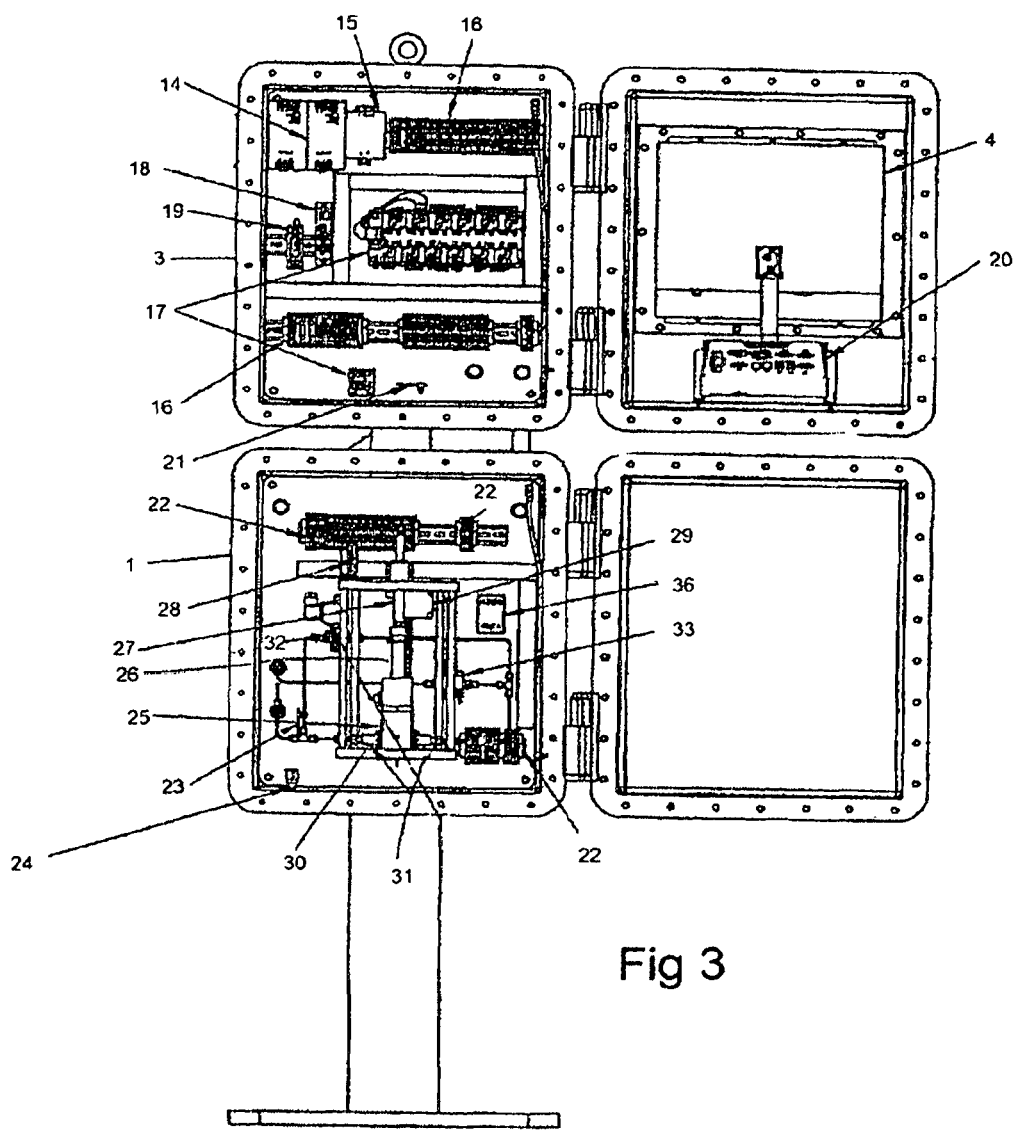
FIG. 3 is a front view of the apparatus of FIG. 1 with the boxes open.

In FIG. 1 a vapour pressure analyser is contained within an explosion-proof box 1. The box 1 is mounted on a stand 2 on which there is mounted a second explosion-proof box 3. The box 3 is mounted above the box 1 with a 40 mm separation between the boxes. On the front of the box 3 there is a touch screen 4. The fronts of boxes 1 and 3 are mounted on hinges 5a,b and 6a,b respectively so that the fronts of the boxes 1 and 3 can pivot through 180° to open the boxes 1 and 3.

In FIG. 2 breathing and draining devices 7 and 8 are mounted on the back of box 1. Communication cable 9 connects boxes 1 and 3 so as to allow power and data transfer between the various electronic devices within the boxes 1 and 3. Boxes 1 and 3 have external enclosure earth bolts 10 and 11 mounted on them to earth the boxes 1 and 3. Earth stud 12 is mounted on frame 2.

Figure 4:
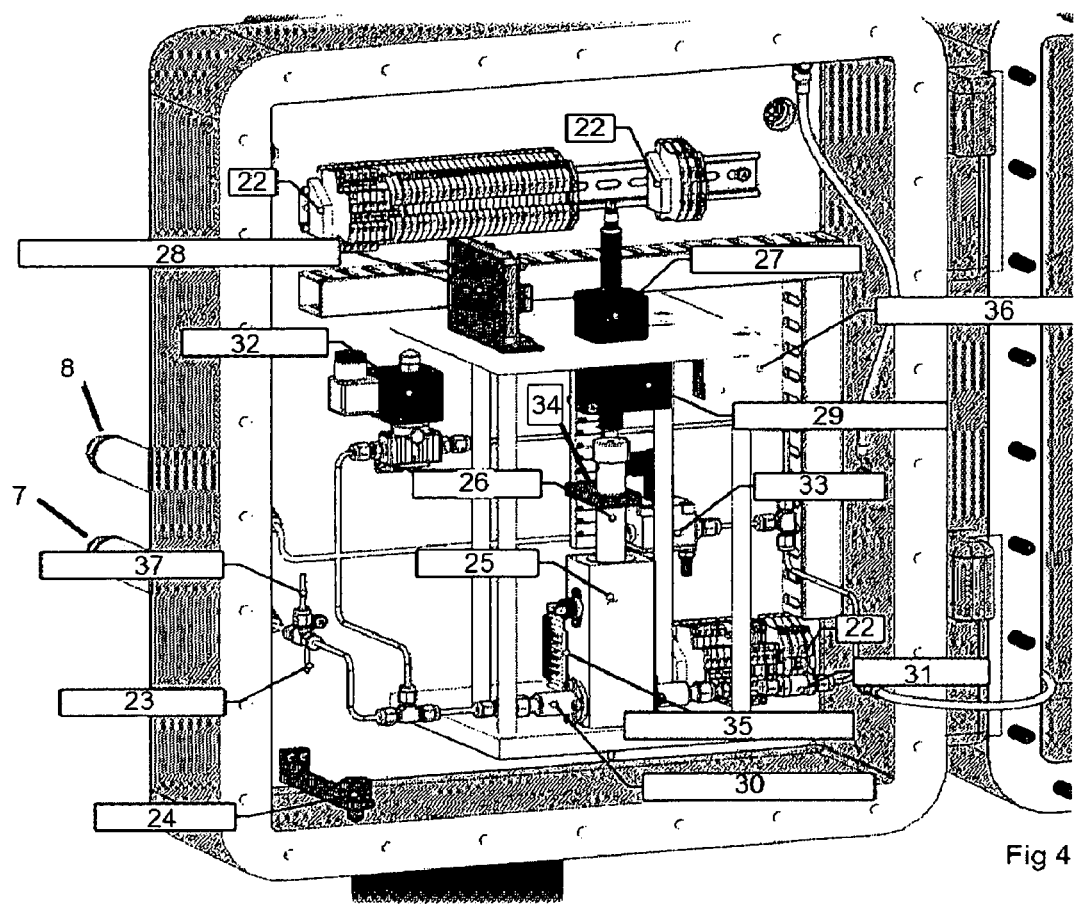
FIG. 4 is a perspective view of the apparatus of FIG. 1.

In FIGS. 3 and 4 box 1 and box 3 are open. In FIG. 3, box 3 contains power supply units 14 and mains power filter 15. The box 3 also contains terminal blocks 16 for mounting components in connection with each other and cable 9 and electronic cards 17. A USB hub 18 and a fibre optic module 19 are also in box 3. Touch screen 4 is mounted on the lid of box 3 and is linked to computer unit 20, which is mounted on the inside of the lid of box 3. There is a temperature sensor 21, which is a resistance temperature detector (RTD), towards the bottom of box 3.

In FIGS. 3 and 4 box 1 also contains terminal blocks 22 and temperature sensor 23. At the low point of box 1 there is a spill sensor 24. The vapour pressure measurement is carried out in a cell comprising a receptacle 25, into which is fitted a piston 26. Mounted on the receptacle 25 is a Peltier cooler 35. Also in box 1 is a heater controlled by a solid state relay 36. The piston 26 is mounted on a linear actuator in the form of a stepper motor 27. The stepper motor 27 is controlled by a controller 28, which receives input from a laser displacement sensor 29 mounted above, and directed at a laser reflector plate 34 mounted on the piston 26. The laser displacement sensor is arranged so as to direct a beam of light onto the laser reflector plate 34 and the reflected beam is processed through a lens onto a detector in the laser displacement sensor 29, with the displacement of the laser reflector plate 34 being related to the position of the reflected beam on the detector. Flow of the sample to the measurement cell is controlled by using valves 30 and 31 with a bypass loop controlled by using valve 32. A flow sensor 33 monitors and controls flow to the cell and an RTD 37 monitors the temperature of the sample inlet.

In use, a sample is drawn from a pipeline in a chemical plant or refinery down a sampling line branching off the pipeline and enters the device through breathing and draining device 7. Before a measurement is made, the chamber is flushed by driving piston 26 down to its maximum extent into receptacle 25 with bypass valve 32 closed and inlet valve 30 and outlet valve 31 open. The chamber is then rinsed by raising and lowering piston 26 to draw sample into the chamber and expel it again. Following the rinse the piston 26 is raised to draw a sample into the chamber and inlet valve 30 and outlet valve 31 closed to trap the sample in the chamber. The chamber is therefore sealed. The piston 26 is then raised in accordance with the expansions required for the test method. Raising the piston 26 expands the chamber and, because the chamber is sealed, therefore results in a liquid/vapour split of the sample, with the volumetric liquid/vapour ratio being determined by the displacement of the piston 26 during the expansion. During the expansions, the position of the piston 26 is measured with laser displacement sensor 29, which provides feedback to stepper motor 27. In that way the expansion is precisely controlled. Once the desired expansion is reached the device pauses to allow time for equilibrium to be reached in the chamber. After the pause the pressure in the chamber is measured by a pressure measurement device in the piston 26. The length of the pause before equilibrium is reached is determined by monitoring the pressure and temperature in the cell and waiting for stable measurements. If the test method requires further expansions, those are carried out in the same way once an equilibrium measurement has been made following the first expansion. Once all expansions are complete, the vapour pressure is calculated in accordance with the test method, for example using a correlation published in the test method, and the result displayed on the screen 4.

Figure 5:
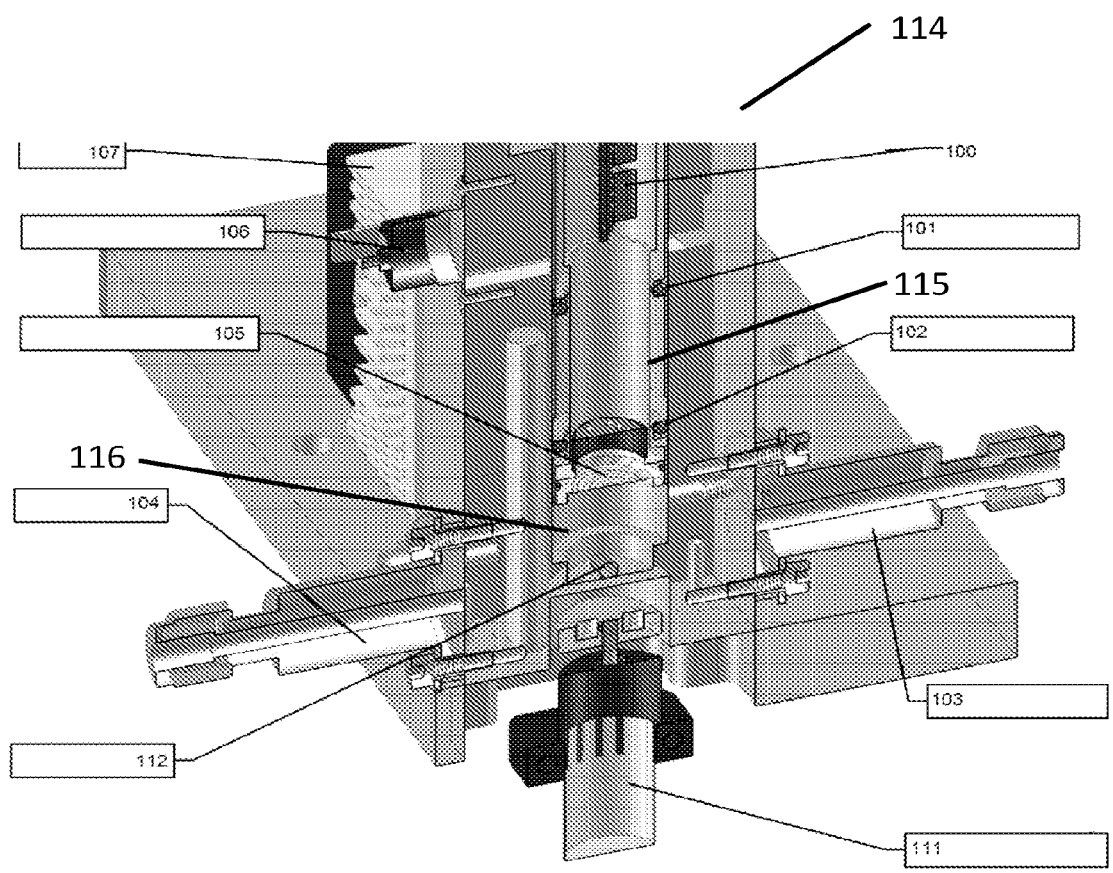
FIG. 5 is a cut-away view of an apparatus according to a second embodiment of the invention.

In FIG. 5 a vapour pressure analyser 114 comprises a sealed chamber 116, which is partially defined by a moveable element in the form of piston 115. The chamber 116 is sealed around the piston 115 by O-rings 101 and 102. The sealed chamber 116 has an inlet 104 and an outlet 103. The lower end of the piston 115 comprises a pressure sensor 105, while the upper part of the piston 115 houses an amplifier 100. Mounted on the outside of the sealed chamber 116 are an over temperature switch 106 and a cooler 107. The chamber comprises an internal sample stirrer in the form of magnetic stirrer bar 112. Below the chamber 116 a stirrer motor 111 is mounted. In use, the stirrer motor 111 drives a pair of magnets in a rotational movement. The magnetic field from the pair of magnets acts on the magnetic stirrer bar 112 to cause it to rotate within the chamber 116, thus agitating the sample.

Figure 6:
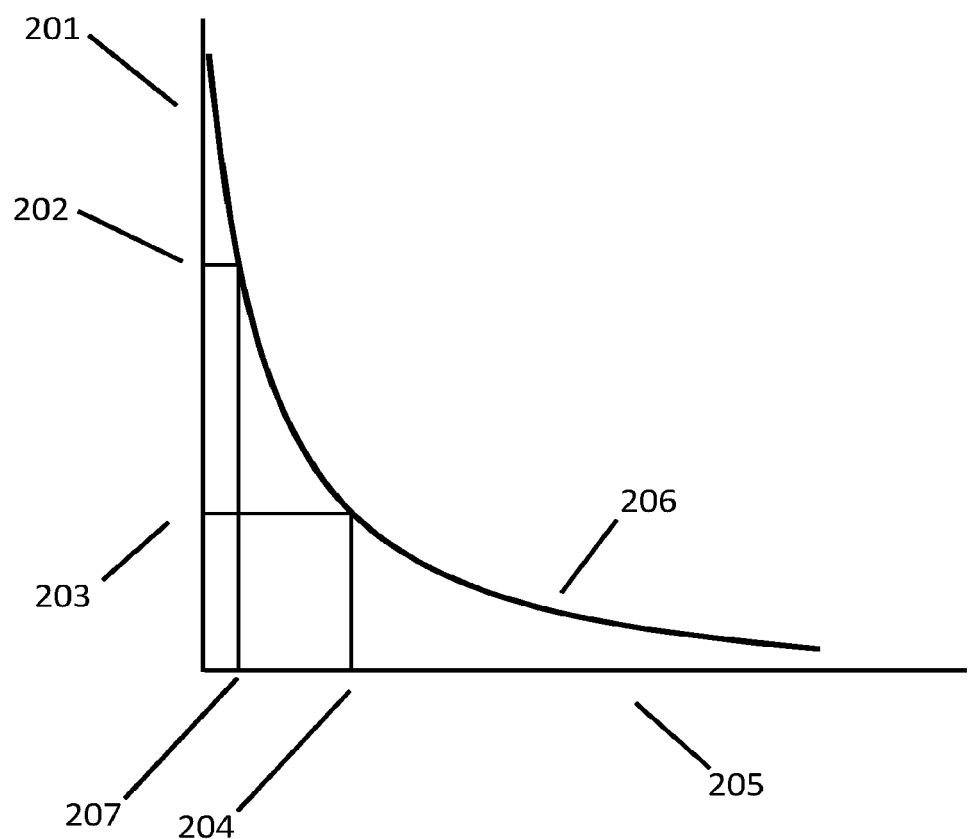
FIG. 6 is a graphical representation of a method according to an embodiment of the invention.

In FIG. 6 a plot 206 of pressure 201 against expansion ratio 205. The plot 206 is obtained by fitting a curve to a series of four pressure measurements taken at four different expansion ratios. The plot 206 can then be used to read off the pressure 202 at an expansion ratio of 0.02:1 207. That pressure may be reported as the TVP. The plot can also be used to read off the expansion ratio 204 at atmospheric pressure (14.7 psia) 203. That ratio may be reported as the GOR. Thus a series of four measurements can be used to predict both TVP and GOR.

Figure 7:
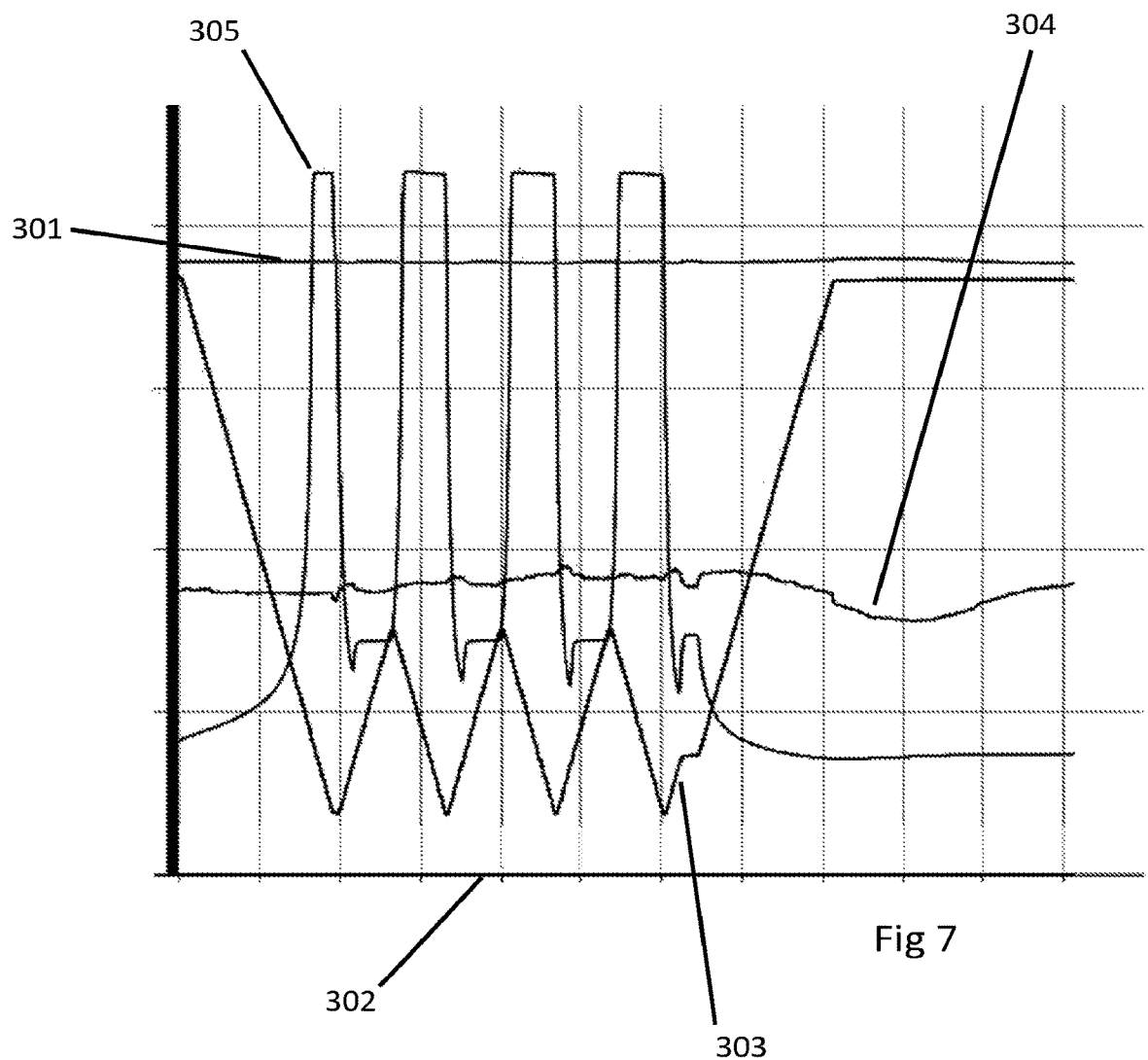
FIG. 7 is a graphical representation of parameters during a flushing cycle of an embodiment of the invention.

In FIG. 7 a flushing cycle is shown plotted against time 302. The temperature 301 and heater power 304 remain approximately constant throughout the cycle. The position of the piston 303 is cycled down and up repeatedly. During the cycle the inlet is closed and the outlet is open as the piston position 303 moves down, so that the chamber is evacuated downstream. While the piston position 303 moves up the outlet is closed and the inlet is open so that flushing fluid is drawn in from upstream. It can be seen that the pressure in the chamber 305 increases markedly as the piston position 303 moves down and the fluid is forced out of the chamber. Because each flush completely empties the chamber on the piston down stroke and because only the flushing fluid required to fill the chamber is drawn in on the piston upstroke, the method is much more efficient in terms of flushing fluid volume that process in which the flushing fluid is flowed through the chamber under pressure.

Whilst the present invention has been described and illustrated with reference to particular embodiments, it will be appreciated by those of ordinary skill in the art that the invention lends itself to many different variations not specifically illustrated herein.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

The invention claimed is:

1. An apparatus for measuring the vapour pressure of a liquid hydrocarbon sample, the apparatus comprising a sealed chamber for receiving the sample; wherein the chamber is at least partially defined by a moveable element such that moving the moveable element alters the volume of the chamber; wherein the apparatus comprises a displacement sensor configured to measure a displacement of the movable element, wherein the displacement sensor is a laser displacement sensor, and wherein the apparatus comprises a motor configured to drive the moveable element and a controller configured to receive a signal from the laser displacement sensor and to control the motor in response to the signal.

2. An apparatus according to claim 1, wherein the moveable element is a piston and the chamber is formed by the piston and a receptacle in which the piston is fitted so as to form a seal between the piston and the receptacle.

3. An apparatus according to claim 1 wherein the apparatus comprises a laser reflector plate coupled to the moveable element and the laser displacement sensor is configured to measure a displacement of the laser reflector plate so as to measure the displacement of the movable element.

4. An apparatus according to claim 1, wherein the apparatus comprises a device for monitoring the temperature of the chamber and a temperature control apparatus to heat or cool the chamber.

5. An apparatus according to claim 4 wherein the device for monitoring the temperature of the chamber is located within the moveable element.

6. An apparatus according to claim 1, wherein the apparatus comprises a pressure sensor to measure the pressure in the chamber, wherein the pressure sensor is located within the moveable element.

7. An apparatus according to claim 1, wherein the apparatus comprises an internal sample stirrer, located within the sealed chamber, to agitate the sample being analysed.

8. An apparatus according to claim 7, wherein the apparatus comprises a magnetic stirrer located inside the sealed chamber and a motor external to the sealed chamber, wherein the motor is configured to drive at least one magnet so as to cause the magnetic stirrer to rotate.

9. An apparatus according to claim 1, wherein the apparatus is contained within an explosion-proof box.

10. A method of measuring the vapour pressure of a liquid hydrocarbon sample, the method comprising:

a. feeding the sample into a sealed chamber, wherein the chamber is at least partially defined by a moveable element;
b. expanding the chamber by displacing the moveable element by a displacement; and
c. measuring the pressure in the chamber;
wherein the displacing of the moveable element includes measuring the displacement with a displacement sensor, wherein the displacement sensor is a laser displacement sensor,
and in which the moveable element is driven by a motor and a controller receives a signal from the displacement sensor and controls the motor in response to the signal.

11. A method according to claim 10, wherein the moveable element is a piston and the chamber is formed by the piston and a receptacle in which the piston is fitted so as to form a seal between the piston and the receptacle.

12. A method according to claim 10 wherein a laser reflector plate is coupled to the moveable element, and the laser displacement sensor measures a displacement of the laser reflector plate so as to measure the displacement of the movable element.

13. A method according to claim 10, wherein the method comprises monitoring the temperature of the chamber and operating a heater or a cooler to maintain the temperature at a desired value.

14. A method according to claim 12, wherein the temperature is monitored using a device located within the moveable element and the pressure is measured using a pressure sensor located within the moveable element.

15. A method according to claim 10, wherein the method comprises stirring the sample between steps b and c.

* * * * *